US00PP22793P3

(12) United States Plant Patent
Meilland

(10) Patent No.: US PP22,793 P3
(45) Date of Patent: Jun. 19, 2012

(54) FLORIBUNDA ROSE PLANT NAMED 'MEIPLUVIA'

(50) Latin Name: *Rosa hybrida*
Varietal Denomination: Meipluvia

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 225 days.

(21) Appl. No.: 12/591,387

(22) Filed: Nov. 18, 2009

(65) Prior Publication Data

US 2011/0119796 P1 May 19, 2011

(51) Int. Cl.
*A01H 5/00* (2006.01)

(52) U.S. Cl. ..... Plt./146

(58) Field of Classification Search ..... Plt./147, Plt./146, 141

See application file for complete search history.

(56) References Cited

U.S. PATENT DOCUMENTS

| | | | | |
|---|---|---|---|---|
| PP8,362 P * | 9/1993 | McGredy, IV | ..... | Plt./143 |
| PP11,485 P * | 8/2000 | Zary | ..... | Plt./147 |
| PP20,767 P3 * | 2/2010 | Schuurman | ..... | Plt./146 |

OTHER PUBLICATIONS

UPOV ROM GTITM Computer Database, GTI Jouve Retrieval Software 2011/01 Citation for 'Meipluvia'.*
Anonymous. "*Rosa* 'Meipluvia' Adobe Sunrise from Conard Pyle" Available at: http://www.conard-pyle.com accessed Mar. 24, 2011.*

* cited by examiner

*Primary Examiner* — Wendy C Haas
(74) *Attorney, Agent, or Firm* — Buchanan Ingersoll & Rooney PC

(57) ABSTRACT

A new and distinct Floribunda rose plant is provided which forms attractive blossoms having a salmon-orange coloration. The blossoms tend to be substantially uniform in appearance and blossoming is displayed on a substantially continuous basis throughout the season. The plant exhibits strong vegetation, a bushy growth habit, and dark green foliage with a semi-glossy aspect. No particular disease concern has been encountered during observations to date. The attractive dark green foliage contrasts nicely with the intense ocher blossom coloration. The new variety is well suited for growing as attractive ornamentation in parks and gardens.

1 Drawing Sheet

Figures 1, 2, 3, 4, 5, 6, 7, 8, 9, 10, 11, 12, 13, 14, 15:
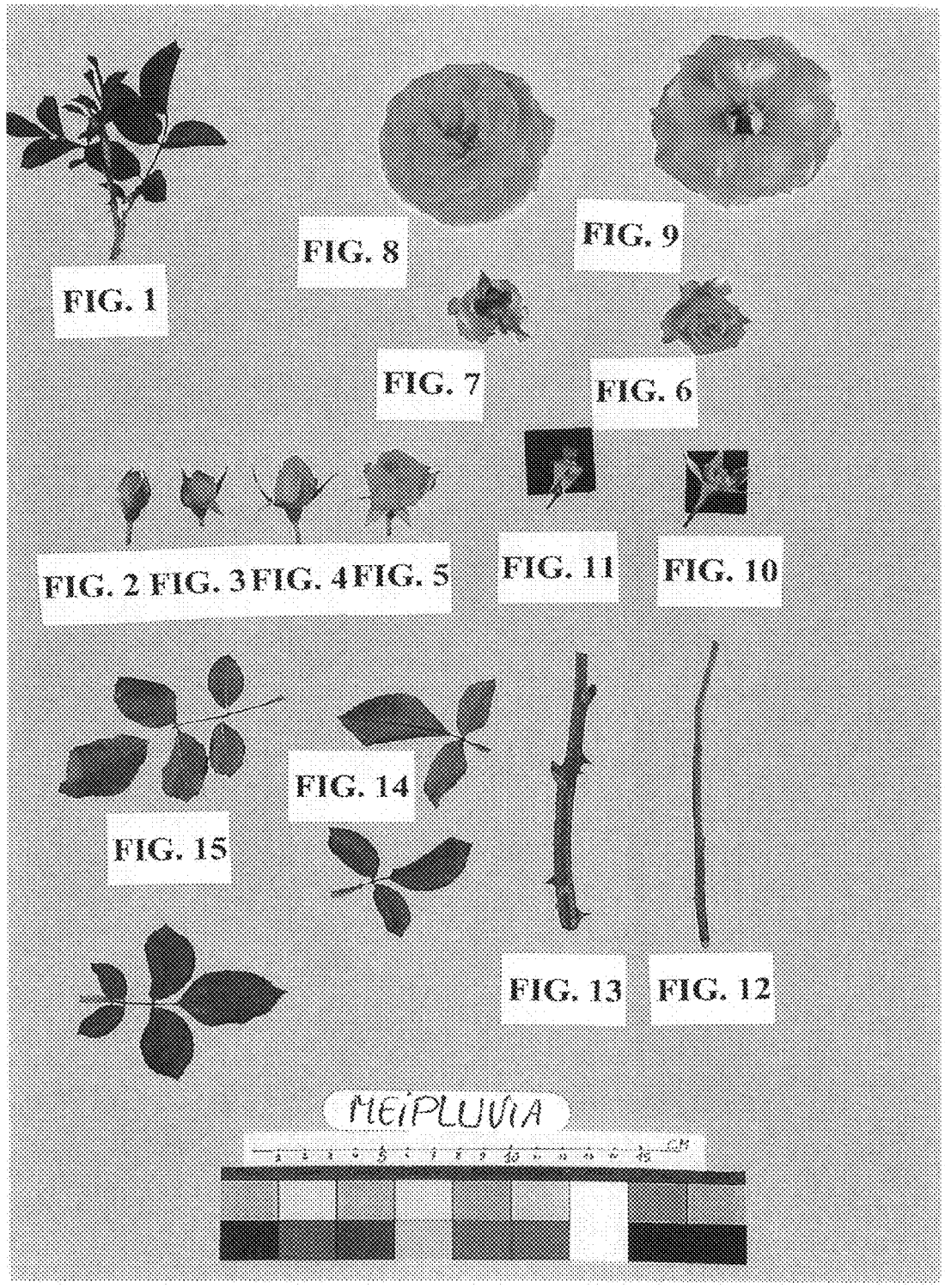

Botanical/commercial classification: *Rosa hybrida*/Floribunda Rose Plant.

Varietal denomination: cv. Meipluvia.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the 'Macivy' variety (U.S. Plant Pat. No. 8,362). The male parent (i.e., the pollen parent) was the 'Meijulita' variety (unpatented in the United States). The parentage of the new variety can be summarized as follows:

'Macivy'×'Meijulita'.

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a bushy growth habit,
(b) abundantly forms on a substantially continuous basis substantially uniform attractive blossoms having a salmon-orange coloration,
(c) forms attractive dark green semi-glossy foliage, (d) displays good resistance to disease, and
(e) is well suited for growing as ornamentation in parks and gardens.

The vegetation is strong and the blooming is precocious. No particular disease concern has been encountered during observations to date. The dark green foliage coloration contrasts nicely with the salmon-orange blossom coloration.

The new variety well meets the needs of the horticultural industry and can be grown to advantage in the landscape where attractive ornamentation is desired.

The new variety can be readily distinguished from its ancestors. For instance, the 'Macivy' variety displays apricot/copper-colored blossoms, and the 'Meijulita' variety displays vermillion-red colored blossoms. When compared to the 'Meidarin' variety (U.S. Plant Pat. No. 13,291), the new variety displays a larger growth habit together with larger blossoms and foliage.

The new variety has been found to undergo asexual propagation in France by a number of routes, including budding, grafting, and the use of cuttings. Asexual propagation by the above-mentioned techniques in France has shown that the characteristics of the new variety are stable and are strictly transmissible by such asexual propagation from one generation to another. Accordingly, the new variety undergoes asexual propagation in a true-to-type manner.

The new variety has been named 'Meipluvia'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately two years of age and were observed during July while budded on *Rosa laxa* understock and growing outdoors at Le Cannet des Maures, Var, France. Dimensions in centimeters are indicated at the bottom of the photograph together with comparative color information.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of leaves with three leaflets—plan view—upper surface (bottom), and—plan view—under surface (top); and FIG. 15—illustrates specimens of leaves with five leaflets—plan view—upper surface (bottom), and—plan view—under surface (top).

DETAILED DESCRIPTION

The chart used in the identification of the colors is that of The Royal Horticultural Society (R.H.S. Colour Chart—1995 or equivalent), London, England. Common color terms are to be accorded their customary dictionary significance. The description is based on the observation of two-year-old plants during October while budded on *Rosa laxa* understock (no particular cultivar name and unpatented in the United States) and growing outdoors at Le Cannet des Maures, Var, France.

Class: Floribunda.

Plant:

*Habit*.—Compact and bushy.

Leaves:

*Stipules*.—Adnate, pectinate, and rather broad, approximately 1.5 cm in length on average, and approximately 0.7 cm in width on average.

*Petioles*.—Upper surface: near Yellow-Green Group 146A in coloration. Under surface: near Yellow-Green Group 146B in coloration. Length: approximately 2.6 cm on average for the terminal leaflet.

*Rachis*.—Upper surface: near Yellow-Green Group 146A in coloration. Under surface: near Yellow-Green Group 146B in coloration.

*Leaflets*.—Number: 3, 5 (most often), and 7. Shape: generally oval with an obtuse base and a somewhat cuspidate tip. Size: the terminal leaflets commonly are approximately 5.2 cm in length on average, and approximately 3 cm in width on average. Serration: small and single (as illustrated). Texture: physically somewhat firm and thick. General appearance: rather dense and semi-glossy on the upper surface. Color (young foliage): upper surface: near Green Group 141A. under surface: near Yellow-Green Group 146C. Color (adult foliage): upper surface: near Green Group 135A. under surface: near Green Group 137C.

Inflorescence:

*Number of flowers*.—Commonly approximately 1 to 5 per stem.

*Peduncle*.—Smooth, approximately 4.2 cm in length on average, and approximately 0.3 cm in diameter on average.

*Sepals*.—Configuration: longish and narrow, tend to be upright at the base, approximately 2.9 cm in length on average, and approximately 0.4 cm in width on average at the widest point.

*Buds*.—Shape: globular. Size: medium. Length: approximately 1.9 cm on average. Width: approximately 1.6 cm on average at the widest point.

*Flower*.—Shape: cup-shaped. Diameter: approximately 7.5 to 8 cm on average. Color (in the course of opening): upper surface: near Red Group 30D suffused with near Orange-Red Group 31B. Under surface: near Yellow-Orange Group 23B suffused with Orange Group 29A. Basal petal spot: on the upper surface near Yellow Group 13A, and on the under surface near Yellow-Orange Group 16A. Color (when fully open): upper surface: near Orange Group 29A slightly suffused with near Yellow-Orange Group 23B. Under surface: near Yellow-Orange Group 23C suffused with near Orange Group 29B. Basal petal spot: on the upper surface near Yellow Group 13A, and on the under surface near Yellow-Orange Group 16A. Fragrance: none. Petal number: commonly approximately 58 to 62 on average under normal growing conditions. Petal shape: rounded with a cuneiform base. Petal texture: consistent and somewhat leathery. Petal arrangement: imbricated, and without petaloids. Petal length: commonly approximately 2.9 cm on average. Petal width: commonly approximately 0.4 cm on average. Petal drop: good with the petals commonly detaching cleanly before drying.

Development:

*Vegetation*.—Strong.

*Blooming*.—Precocious, and substantially continuous with the formation of substantially uniform blossoms.

*Resistance to diseases*.—No particular disease concern has been encountered during observations to date.

I claim:

1. A new and distinct Floribunda rose plant characterized by the following combination of characteristics:

(a) exhibits a bushy growth habit, (b) abundantly forms on a substantially continuous basis substantially uniform attractive blossoms having a salmon-orange coloration, (c) forms attractive dark green semi-glossy foliage, (d) displays good resistance to disease, and (e) is well suited for growing as ornamentation in parks and gardens; substantially as herein shown and described.

* * * * *

MEIPLUVIA